(12) United States Patent
Sejrsen et al.

(10) Patent No.: US 7,077,002 B2
(45) Date of Patent: Jul. 18, 2006

(54) METHOD AND AN APPARATUS FOR MEASURING FLOW RATES

(75) Inventors: Per Sejrsen, Frederiksborgvej 139 A, Roskilde (DK) DK-4000; Mette Midttun, Nordhojen 5, Roskilde (DK) DK-4000

(73) Assignees: Per Sejrsen, Roskilde (DK); Mette Midttun, Roskilde (DK); Jens Hove, Copenhagen K (DK); Henrik Kruckow, Helsinge (DK); Thorkild Bog-Hansen, Hellerup (DK)

( * ) Notice: Subject to any disclaimer, the term of this patent is extended or adjusted under 35 U.S.C. 154(b) by 663 days.

(21) Appl. No.: 10/168,111

(22) PCT Filed: Dec. 18, 2000

(86) PCT No.: PCT/DK00/00704

§ 371 (c)(1),
(2), (4) Date: Oct. 28, 2002

(87) PCT Pub. No.: WO01/43629

PCT Pub. Date: Jun. 21, 2001

(65) Prior Publication Data
US 2003/0139676 A1    Jul. 24, 2003

(30) Foreign Application Priority Data
Dec. 17, 1999  (DK) ............................. 1999 01815

(51) Int. Cl.
*G01F 1/68*   (2006.01)
(52) U.S. Cl. ................. 73/204.26; 73/204.12
(58) Field of Classification Search ............ 73/204.26, 73/204.12
See application file for complete search history.

(56) References Cited

U.S. PATENT DOCUMENTS

| 4,354,504 A | 10/1982 | Bro |
| 4,859,078 A | 8/1989 | Bowman et al. |
| 5,844,123 A * | 12/1998 | Marsh et al. ............... 73/19.12 |

FOREIGN PATENT DOCUMENTS

| DE | 33 09 093 A1 | 9/1984 |
| EP | 0 157 962 A1 | 10/1985 |

(Continued)

OTHER PUBLICATIONS

Siggard-Andersen et al., "Model for Calculating Skin Perfusion From Hat Flux Measured with a Double heated Transcutaneous $pO_2$ Electrode", *Scand J Clin Lab Invest*, 48, Sppl. 189, pp. 21-25 (1988).

(Continued)

*Primary Examiner*—Harshad Patel
(74) *Attorney, Agent, or Firm*—Browdy and Meimark, PLLC

(57) ABSTRACT

A device for measuring the flow rate of a fluid confined by a wall member, and wherein the device comprises contacting apparatus for contacting the wall member, the contacting apparatus being formed of a material having a first heat transfer coefficient so that heat may be exchanged between the wall member and the contacting apparatus. The device further comprises heating apparatus for supplying heat to and draining heat from the contacting apparatus so that heat is being supplied to the wall member when heat is being supplied to the contacting apparatus and so that heat is being drained from the wall member when heat is being drained from the contacting apparatus. Bridging apparatus for providing thermal contact between the heating apparatus and the contacting apparatus are provided.

20 Claims, 9 Drawing Sheets

FOREIGN PATENT DOCUMENTS

| | | |
|---|---|---|
| EP | 0 368 296 A1 | 5/1990 |
| EP | 0 599 813 A2 | 6/1994 |
| EP | 0 656 760 B1 | 6/1995 |
| GB | 2 203 835 A | 10/1988 |
| WO | WO 83/01510 A1 | 4/1983 |
| WO | WO 86/03118 A1 | 6/1986 |
| WO | WO 89/11083 A1 | 11/1989 |
| WO | WO 91/12765 A1 | 9/1991 |
| WO | WO 92/12539 A1 | 9/1992 |
| WO | WO 94/02065 A1 | 2/1994 |
| WO | WO 95/05115 A2 | 2/1995 |

OTHER PUBLICATIONS

Jaszczak, *Blood Flow Rate, Temperature, Oxygen Tension and Consumption in the Skin of Adults Measured by a Heated Microcathode Oxygen Electrode*, pp. 2-19, Lægeforeningens Forlag: 1988.

Jaszczak et al., "Determination of Skin Blood Flow by $^{133}$Xe Washout and by Heat Flux from a Heated tc-Po$_2$ Electrode", *Acta Anaesthesiol Scand*, vol. 28, pp. 482-489 (1984).

Midttun et al., "Blood Flow Rate During Orthostatic Pressure Changes in the Pulp Skin of the First Toe", *Eur J Vasc Endovasc Surg*, vol. 13, pp. 278-284 (1997).

Sejrsen et al., "Exercise and the Circulation in health and Disease", The Copenhagen Muscle Research Centre: First CMRC Conference (Oct. 29-Nov. 1, 1995).

Midttun et al., "Heat-Washout: A New Method for Measuring Cutaneous Blood Flow Rate in Areas with an Without Arteriovenous Anastomoses", *Clinical Physiology*, vol. 16, pp. 259-274 (1996).

\* cited by examiner a)

b)

Series 1-4: Measurements on the forearm at various temperature levels.
Series 5: Measurements on the forearm during blood flow cessation.

Series 1-4: Measurements on the pulp of the thumb at various temperature levels.
Series 5-6: Measurements on the pulp of the thumb during blood flow cessation.

Series 1: Measurements on the pulp of the thumb at various positions.
Series 2: Measurements on the pulp of the thumb with the other hand in ice-water.

Thermistor: RS (Radio Parts) type 151-221

METHOD AND AN APPARATUS FOR MEASURING FLOW RATES

The present invention relates to a method and a device for measuring flow rates of a fluid being confined by a substantially non-penetrable wall member and relates in particular to measuring flow rates of blood streaming in tissue.

BACKGROUND FOR THE INVENTION AND INTRODUCTION TO THE INVENTION

Today measuring of blood flow rates in the human body is typical performed by adding $^{133}$Xe to the tissue and afterwards measuring locally the decay of radioactive radiation, which experimentally has been correlated with the flow rate of the blood. This known method is referred to as the $^{133}$Xe-wash-out method as the decay of radiation is governed by transportation of the radioactive isotope by the blood, i.e. the radioactive isotope is said to be washed out from the tissue.

This method has some major disadvantages:

The $^{133}$Xe-wash-out method requires a frequent delivery of the radioactive isotope $^{133}$Xenon which involves a considerable expenditure, about 1000 Kr. (Danish crowns) every 14. day.

The apparatus for registration of $^{133}$Xenon wash-out has a price of about 60,000 Kr.

As $^{133}$Xenon is a radioactive isotope it exposes ionising radiation to the tissue in which it is deposited. This is undesirable and the $^{133}$Xe-wash-out method has for ethical—and perhaps also for medical—reasons not been used for pregnant women and child patients.

An attempt to overcome the problems related to the $^{133}$Xe-wash-out method has been proposed by using heat instead of the radioactive isotope. In this method, which for instance is disclosed in M. Midttun, P. Sejrsen and M. Colding-Jørgensen, Heat-wash-out: A new method for measuring cutaneous blood flow rate in areas with and without arteriovenous anastomoses; Clinical Physiology (1996), 16, 259–274, heat is applied locally to the skin until a steady temperature of the tissue has established. After the steady temperature has been established, the heat supply is turned off where after the temperature decrease in time is recorded.

On the basis of the recorded temperature decrease in time the blood flow rate is determined. Correlation of the temperature decrease and the blood rate in the heat wash-out method is based on comparing the temperature decrease with results determined by the $^{133}$Xe-wash-out method.

A major disadvantage of the heat wash-out method is that the wash-out of heat is dependent on at least the temperature of the blood, tissue and the surroundings thereto. This implies that the flow rate of the blood—and in general the fluid to be measured—increases with increasing temperature and decreases with decreasing temperature.

By only applying heat to the tissue to be measured the flow rate detected by the temperature decrease does not correspond to the undisturbed flow rate, i.e. the flow rate of the blood at normal tissue temperature.

Another problem involved in measuring flow rate by heat wash-out is that the surface of the skin—or in general the wall member—where heat is applied and the surrounding area F has to be held at a temperature guaranteeing that heat at least during the heat wash-out phase is not drained from the skin (or the wall member) to the ambience in order to have a correct measure of the transportation of heat done by the blood (or the fluid).

Furthermore, the correlation between the flow rate and the temperature of the tissue and thereby the fluid to be measured has been focused on in the above mentioned reference (Midttun et al, 1996) using the $^{133}$Xenon-wash-out method in comparison with the heat wash-out method.

Probes for simultaneous measuring the $p_{tc}O_2$, $p_{tc}CO_2$ and the blood flow rate in the tissue beneath the probes are disclosed in the International Patent Application WO 83/01510 and in the European Patent no. EP 0 656 760. The probes disclosed therein both evaluate the flow rate of the blood by thermostating the surface of the tissue to a constant temperature and then evaluate the blood flow rate on the basis of the heat dissipated constantly in the probe during measuring and on the basis of an estimated arterial temperature or deep body temperature.

One major problem in connection with these prior art probes is the estimation of the deep body temperature which is not directly available. Another major problem in connection with the prior art probe is connected to the temperature dependency of the flow rate of blood. When only a one sided measuring technique is applied, i.e. only heat wash-out, the flow rate determined is not the flow rate of the blood being present during undisturbed conditions, i.e. when heat is not exchanged actively by the probe.

Further apparatuses are known from U.S. Pat. No. 4,859,078 which discloses an apparatus for the non-invasive measurement of thermal properties and perfusion rates of biomaterials, and from DE 33 09 093 that discloses an apparatus for measuring the blood flow in the skin.

BRIEF DESCRIPTION OF THE INVENTION

These problems have been solved by means of the present invention, which provides an apparatus for measuring the flow rate of a fluid confined by a wall member, which apparatus comprises contacting means for contacting the wall member, the contacting means being formed of a material having a first heat transfer coefficient so that heat may be exchanged between the wall member and the contacting means, heating means for supplying heat to and draining heat from the contacting means so that heat is being supplied to the wall member when heat is being supplied to the contacting means and so that heat is being drained from the wall member when heat is being drained from the contacting means, and bridging means for providing thermal contact between the heating means and the contacting means.

In the present context the phrase "confined by a wall member" is to be understood in a broad context, for instance in the sense that there is an interface which in general is non-penetrable or substantial non-penetrable by the fluid in question and below which the fluid is streaming. Thereby, also the meaning of said phrase covers the situation in which a fluid flows through a fluid-penetrable matter, such as human tissue, situated below the outer skin surface.

The heating means according to the present invention must preferably be adapted to be set at a temperature being higher or lower than the undisturbed temperature of the tissue or the fluid so as to be able to supply or drain heat from the wall member in a controllable manner. Therefore, the heating means is/are active cooling means which temperature is actively controllable.

The contacting means is preferably means being so manufactured that it/they is/are adapted to the surface to which it/they is/are to contact. In a particular preferred embodiment of the present invention the contacting means is a circular shaped disc having a heat transfer coefficient enabling a good transfer of heat. A good transfer of heat in this context is characterised in that the temperature gradient normal to the surface of the disc and through the disc is so that the temperature difference between the surface of the disc not contacting the wall and the surface of the disc contacting the wall is smaller than 1° C. such as smaller than 0.5° C. preferably smaller than 0.25° C.

Preferably the contacting means is made of metal such as iron, aluminium, copper, silver or gold.

The apparatus according to the present invention provides by using a combination of heat wash-out and heat wash-in an apparatus giving absolute figures of blood flow rate. The flow rate is in a preferred embodiment of the invention provided at the temperature level present before measurement by averaging two measurements with equal or substantial equal heating and cooling. The apparatus thereby provides a solution to the problems connected with the heat wash-out method and also problems connected with the $^{133}$Xe-wash-out method, and the apparatus according to the present invention therefore has a potential to replace the both prior art methods for measurement of cutaneous blood flow rate.

In a broad aspect of the present invention the apparatus is suitable for measuring flow rate of a fluid confined by a non-penetrable or substantially non-penetrable wall member.

In a specific aspect of the present invention the apparatus is suitable for measuring cutaneous blood flow rates in medical research, in examination of patients, in control of effect of treatment, in supervision of patients, and in scientific investigation within circulation physiology, exercise physiology, and temperature regulation.

A great advantage is achieved by using heat as a tracer in the wash-out method. Compared to the use of $^{133}$Xe as a tracer the diffusion of heat through for instance human skin is about 100 times faster than diffusion of $^{133}$Xe. This faster diffusion provides a possibility for measuring blood flow rates in the thumb pulp, which contains large arterio-venous shunt vessels with a diameter of 40 to 50 μm.

By combining heat wash-out with heat wash-in as done in the apparatus according to the present invention measurement of the flow rate in for instance the skin of the forearm and/or thumb pulp is made possible in such a manner that the temperature dependency of the flow rate is removed.

A major advantage of the apparatus according to the present invention is it's applicability to measure blood flow rates quantitatively in cutaneous tissue areas with arterio-venous shunt vessels which is not possible by the $^{133}$Xe-wash-out technique or by venous occlusion plethysmography (Midttun et. al. 1996, cf. above). The cause for this applicability is that the diffusibility of heat is about 100 times higher than diffusibility of $^{133}$Xe yielding a possibility for equilibrium of heat between tissue and blood during the wash-out/wash-in process.

Furthermore, it is possible to estimate blood flow rates quantitatively in cutaneous areas with solely capillaries as an average value between a registration during heat wash-out and a registration during heat wash-in. In areas with arterio-venous shunt vessels controlled by the central thermo regulation there will be an almost constant blood flow rate at various temperatures of the probe, when the subject is in a positive heat balance.

By applying both heat wash-out and heat wash-in some of the advantages are: Less expenses to the measurement apparatus, and to the delivery of $^{133}$Xe, and the time of registration needed is essentially reduced: such as from 60–90 min to 5–10 min.

The heating means is/are means adapted to supply and/or drain heat from the contacting means, and the apparatus comprises bridging means for providing thermal contact between the heating means and the contacting means. The heating means is/are in such situations situated in a distance from the contacting means.

Preferably the bridging means is/are being arranged so that thermal contact between at least one of the at least one heating means and the contacting means is established when the bridging means is/are arranged in thermal contact with the heating means and the contacting means whereby supply/drain of heat to the contacting means may conveniently be controlled by enabling/disabling direct mechanical connection between the contacting means and the heating means.

The probe may preferably comprise encapsulating means for encapsulating the heating means and for encapsulating partly the contacting means, the encapsulating means has an outer surface whereof at least a part of it is exposed to the surroundings when the contacting means is contacting the wall member.

The encapsulating means serves conveniently the purpose of defining a compartment in which the different components of the probe such as heating means, bridging means and contacting means may be arranged. Besides serving this practicable purpose the encapsulating means may preferably also play a heat-exchanging role. In such situations the encapsulating means is/are being formed of a material having a second heat transfer coefficient so that heat may be exchanged with the surroundings. Furthermore the encapsulating means may have a predetermined heat capacity so that time response of the probe may be varied.

In a particular preferred embodiment of the apparatus according to the present invention the heating means is/are situated in the encapsulating means or in the vicinity there to and thermal contact between the contacting disc and the heating means is provided by means of the bridging means. By such an arrangement heat exchange between the encapsulating means and its surroundings and between the contact disc and the encapsulating means is made controllable as the temperature of the encapsulating means may be set by the heating means.

That heat can be exchanged between the encapsulating means and its surroundings. As the temperature of the encapsulating means can be set provides a possibility of controlling the heat exchange between the contacting means and the wall in these preferred embodiments. For instance if heat is desired to be transferred only from the disc to the wall and not to the encapsulating means the temperature of the encapsulating means is set so that the temperature difference between these two parts is small or zero. Furthermore, if it is desired that the temperature progression of the contacting means is substantially only dependent on heat wash-in/heat wash-out then the temperature of the encapsulating means must to some extend follow that of the contacting means which preferably may be provided by the heat conductability of the encapsulating means.

In order to register the temperature in the probe the apparatus may further comprise sensor means for sensing the temperature of the contacting means. Preferably, the sensor means is situated in the contacting means so as to measure a temperature being as close as possible to the temperature of the wall member. Another arrangement of the sensor means for sensing the temperature of the contacting means is possible as the temperature sensed by a sensor located in a distance of the contacting means may be correlated such as to express the temperature of said contacting means.

In order to sense the temperature of the encapsulating means, the apparatus may in a preferred embodiment of the present invention further comprise sensor means for sensing the temperature of the encapsulating means. Such sensor means may provide the input on which controlling, such as thermosetting, of the encapsulating means is based. The thermosetting may preferably be such that the temperature of the encapsulating means is substantially equal to or equal to the temperature of the contacting means so that the heat is not exchanged between the encapsulating means and the contacting means. The number of sensor means is one, preferably two and in some preferred cases more than two.

Preferably the sensor means is/are of a thermistor type such as a resistor having a resistance that varies with temperature such as NTC-resistor types and/or PTC-resistor types. Different types of thermistors may be applied for sensing. For instance a NTC-resistor may be applied for sensing the temperature of the contacting means and a PTC-resistor type may be applied for sensing the temperature of the encapsulating means.

In a preferred embodiment of the apparatus according to the present invention the bridging means provides thermal contact between the heating means and the encapsulating means when arranged so that thermal contact between the contacting means and the heating means is not provided.

The apparatus may comprise means adapted to control the temperature of the encapsulating means in such a manner that the temperature of the encapsulating means is at least substantially equal to the temperature of the surface of the wall contacted by the contacting member. Such control means may preferably be an electronic unit controlling the heat dissipated in the heating means and receiving signals relating to the sensed temperature of the contacting means and the encapsulating means. The electronic unit may then determine the amount of heat dissipated in the heating means so that the temperature difference between the encapsulating means and the contacting means stays within a predetermined interval said interval might have limits coinciding.

In a preferred embodiment of the invention the contacting means has at least two regions with different heat transfer coefficient at least concentrically arranged and thereby defining an inner and an outer region. In a particular preferred embodiment the heat transfer coefficient of the outer region of the contacting means is smaller than heat transfer coefficient of the inner region of the contacting means. Such an arrangement helps to control the heat transfer through the contacting means. For instance when the outer region is provided a heat transfer coefficient being higher, such as many times higher, than the heat transfer coefficient of the inner region heat transfer through the inner region is substantially one-dimensional in the sense that only a limited amount of heat will be exchanged with the outer region.

As the result of applying the apparatus according to the present invention is to apply/drain heat to/from the wall member the apparatus preferably comprises processor means adapted for controlling the heating means so that the heat supplied by and/or drained by heating means is supplied/drained in a predetermined manner. The processor means may be a purpose designed electronic circuit or it may be a computer such as a personal computer equipped with a suitable interface for interfacing with the electronics applied power to the heating means and for interfacing with the sensor means.

Furthermore, the apparatus has to be able to both supply and drain heat which feature preferably may be provided in a preferred embodiment of the probe, in which the heating means comprises at least two heating means; one heating means for supplying heat and one heating means for draining heat. Preferably these heating means may both be of a Peltier type as such type may perform both tasks.

In general, the heating means may preferably be of a Peltier type. In a preferred embodiment two Peltier elements are applied for supplying and for draining heat. The heating means for heating and cooling the contacting means is/are preferably placed in the encapsulating means of the probe, also in case where other heating means than Peltier types are used.

In another aspect of the present invention a method for measuring the flow rate of a fluid confined by a wall member is provided. This method comprises
  supplying heat locally to the wall member until a prescribed upper temperature relating to the temperature of the locally heated wall member is achieved,
  recording progression of a temperature relating to the wash-out of heat by the fluid,
  draining heat locally from the wall member until a prescribed lower temperature relating to the locally cooled wall member is achieved,
  recording the progression of a temperature relating to the wash-in of heat by the fluid,
  determining the flow rate of the fluid based on the progression of temperature during wash-in and wash-out.

Supply of heat may in the present context be construed as heating resulting in a temperature increase, but should also be construed to cover the situation in which heat is supplied not resulting in a temperature increase, i.e. a steady state. The construing is similar in the case of draining.

In a preferred aspect of the method according to the present invention the temperature progression relating to the wash-out and wash-in of heat by the fluid are temperatures determined/sensed at the surface of the wall member at the position where heat is supplied/drained.

Preferably the prescribed upper temperature reached when supplying heat is the steady state temperature. This might for instance be the case in which the amount of heat supplied is constant in time, which will result in establishment of a steady state condition in which the heat applied to the wall is balanced by the amount drained by the fluid.

The above discussion is also valid for draining, as this is just a matter of in which direction heat is transported. Accordingly, the prescribed lower temperature reached when draining heat might be the steady state temperature.

It might be of advantage to be able to control the supply/drain of heat to/from the wall member in time, for instance if a measurement is to be performed in an environment in which sudden changes of temperature is not allowed or where certain temperatures of the wall member, such as the upper/lower temperature, are allowed only for a short duration. So, in a preferred embodiment of the method heat is drained from the wall member in such a manner that the temperature of the wall member evolves in a predetermined manner and/or wherein heat is supplied to the wall member in such a manner that the temperature of the wall member evolves in a predetermined manner.

In yet another preferred embodiment of the method said method further comprises the step of controlling the temperature above the wall member during heat wash-out in such a manner that heat is substantially not drained from the wall member to the exterior. This step serves the purpose of making the method more reliable in the sense that by controlling the temperature above the wall member the heat exchange between the exterior and the wall member may be controlled.

Similar, the method may further comprise the step of controlling the temperature above the wall member during heat wash-in in such a manner that heat is substantially not supplied to the wall member from the exterior.

Preferably the upper temperature is 1° C., such 2° C., preferably 3° C. such as 4° C., preferably 5° C. above the temperature of the wall member before heat is initially supplied.

Preferably the lower temperature is 1° C., such 2° C., preferably 3° C. such as 4° C., preferably 5° C. below the temperature of the wall member before heat is initially drained.

The temperature of the wall member, before heat is initially supplied/drained, is normally referred to as the normal basis temperature.

In yet another aspect of the method according to the present invention the method also comprises steps for determining/calculating the actual flow rate based on the recorded temperature progressions.

This aspect is embodied in a method for determining the flow rate comprising the step of the first method aspect and further comprising the steps of
  determining a flow rate constant relating to heat wash-in and a flow rate constant relating to heat wash-out, the determination of the flow rate constants being based on the recorded temperatures progressions corresponding respectively to heat wash-in and heat wash-out,
  determining a heat wash-in fluid flow rate relating to flow rate during heat wash-in; the determination of the fluid flow rate is being based on the corresponding flow rate constant,
  determining a heat wash-out fluid flow rate relating to flow rate during heat wash-out; the determination of the fluid flow rate is being based on the corresponding flow rate constant,
  determining a mean fluid flow rate based on averaging the heat wash-in and heat wash-out fluid flow rate.

It should be noted that the chain of step comprised in the method of determining the flow rate is only expressive of a preferred embodiment and is not to be construed as being statutory. The different steps may conveniently be implemented and combined with the method for measuring the flow rate in a way where each step of the determining method is executed when the data necessary for execution has been made available by the method for measuring.

Furthermore, the present invention relates to an apparatus, a probe, for determining the flow rate of a fluid which apparatus comprises the means and/or features according to one or more of the different embodiments of the apparatus and utilises one or more of the embodiments of the method for measuring and determining flow rates.

In that specific case—and also in the general case—the apparatus for determining the flow rate preferably further comprises processor means adapted to perform the determination of the flow rate constants and the mean flow rate.

The apparatus is in general preferably produced of ordinary mechanical and electrical components and it is preferably produced so as to make the processing of the data obtained during measurement easy handable in an accompanying computer program.

The apparatus may be made easy to use, so that due to its simplicity in use it is usable for doctors, technicians, nurses, and non medical personnel working with circulatory physiology, theoretical gymnastics, and exercise physiology.

BRIEF DESCRIPTION OF THE DRAWINGS

In the following the invention and in particular preferred embodiments thereof will be described in greater details in connection with the accompanying drawings in which.

GENERAL DESCRIPTION OF THE INVENTION

Figure 1:
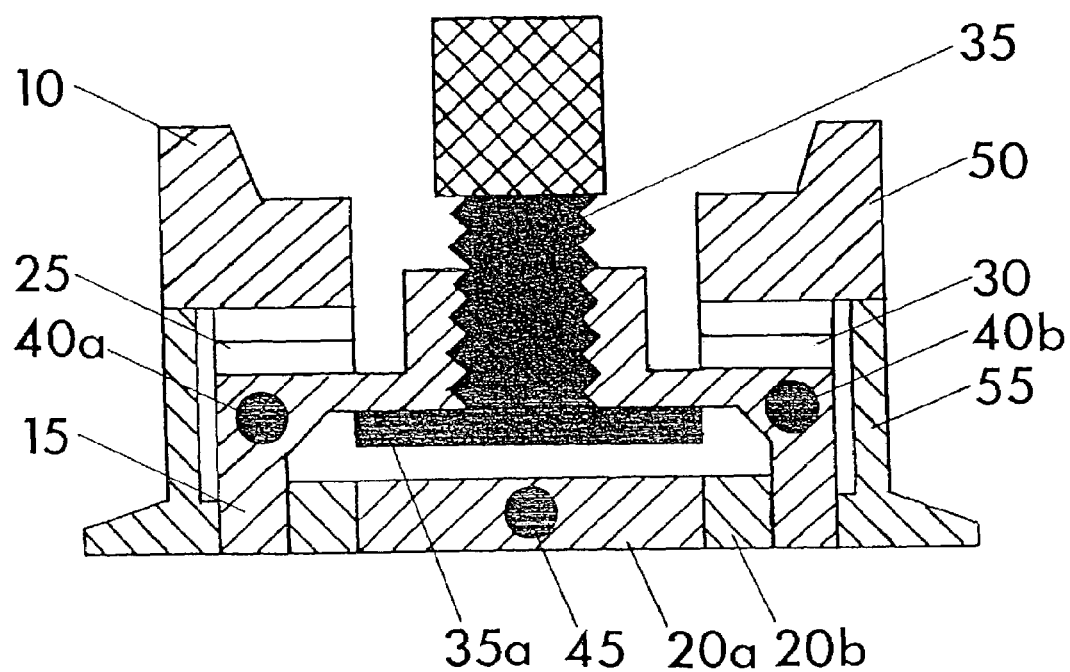
FIG. 1 shows a cross sectional view of a first preferred embodiment of the probe for measuring blood flow.
Figure 2:
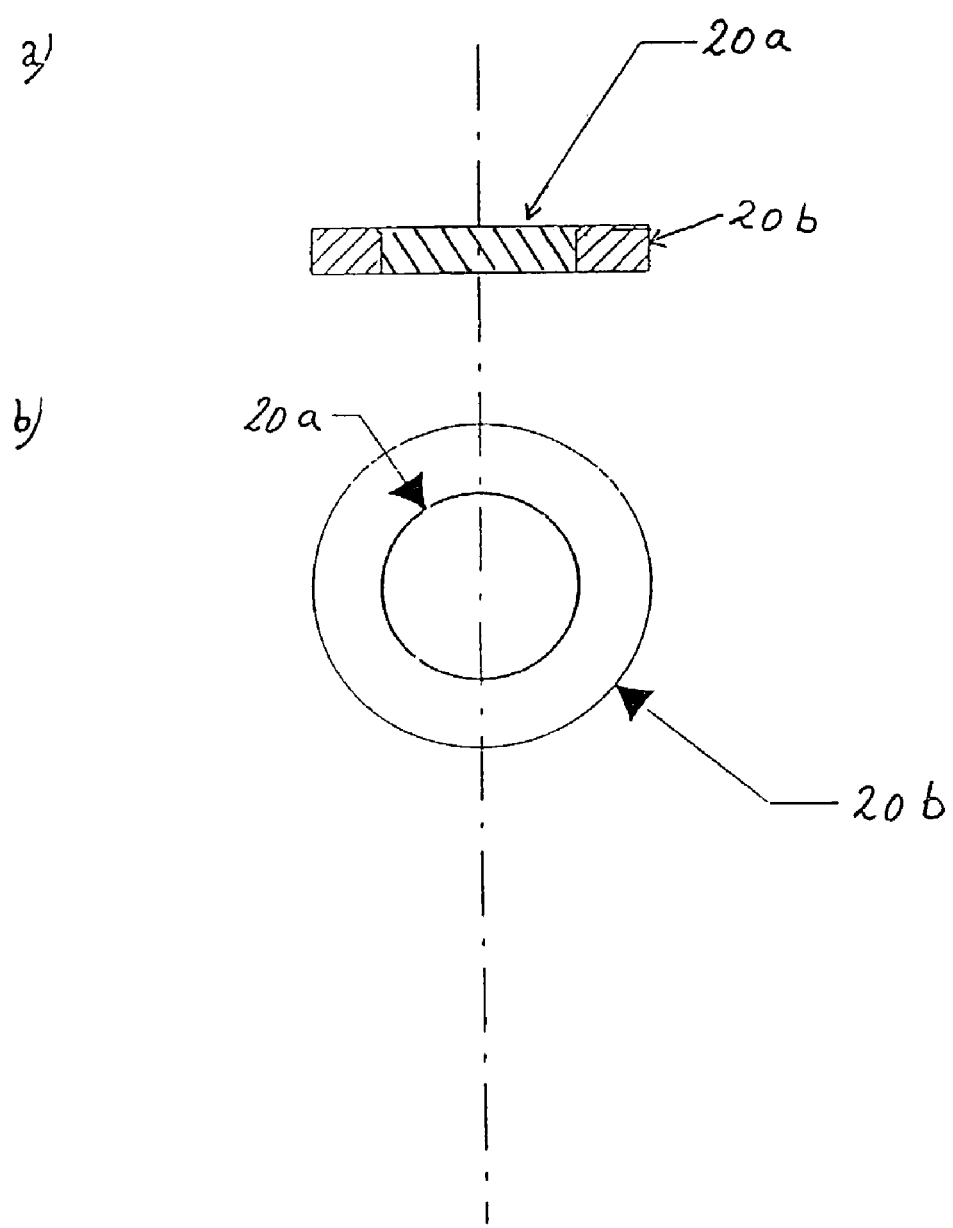
FIG. 2 shows the measuring disc comprised in the probe of FIG. 1; FIG. a) is a side view of the disc and FIG. b) is a top view of the disc.
Figure 3:
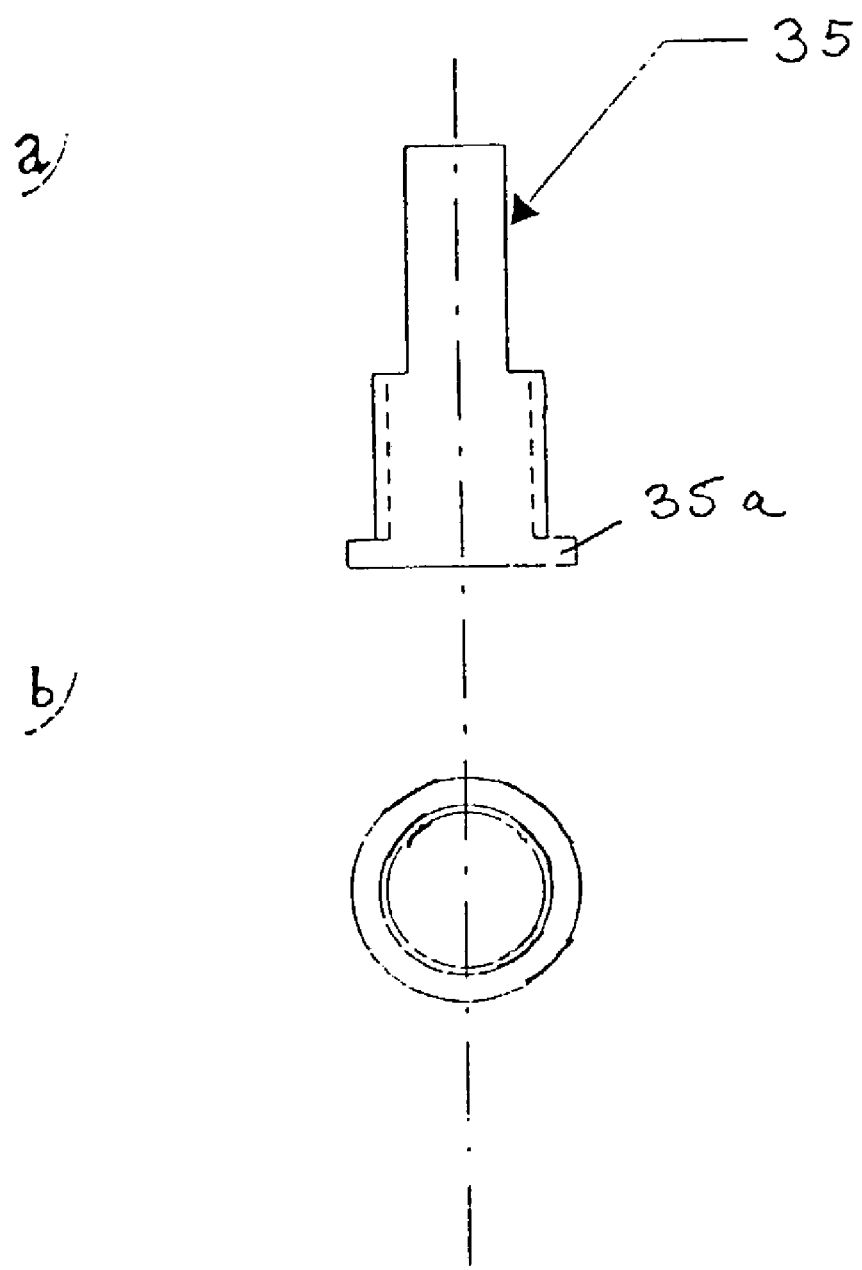
FIG. 3 shows the moveable bridge comprised in the probe of FIG. 1; FIG. a) is a side view of the bridge and FIG. b) is a top view of the bridge.
Figure 4:
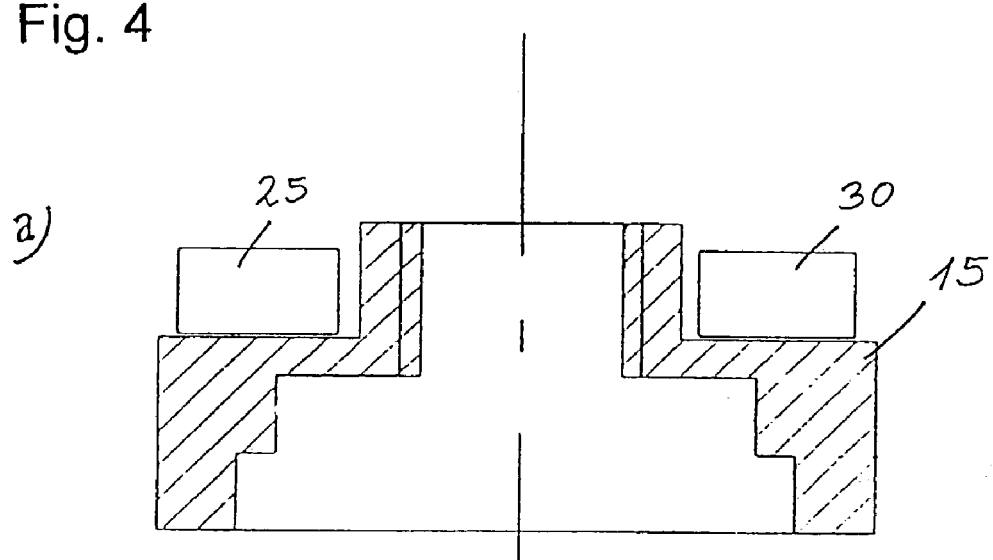
FIG. 4 shows the cap of the probe of FIG. 1; FIG. a) is a side view of the cap and FIG. b) is a top view of the cap.
Figure 4:
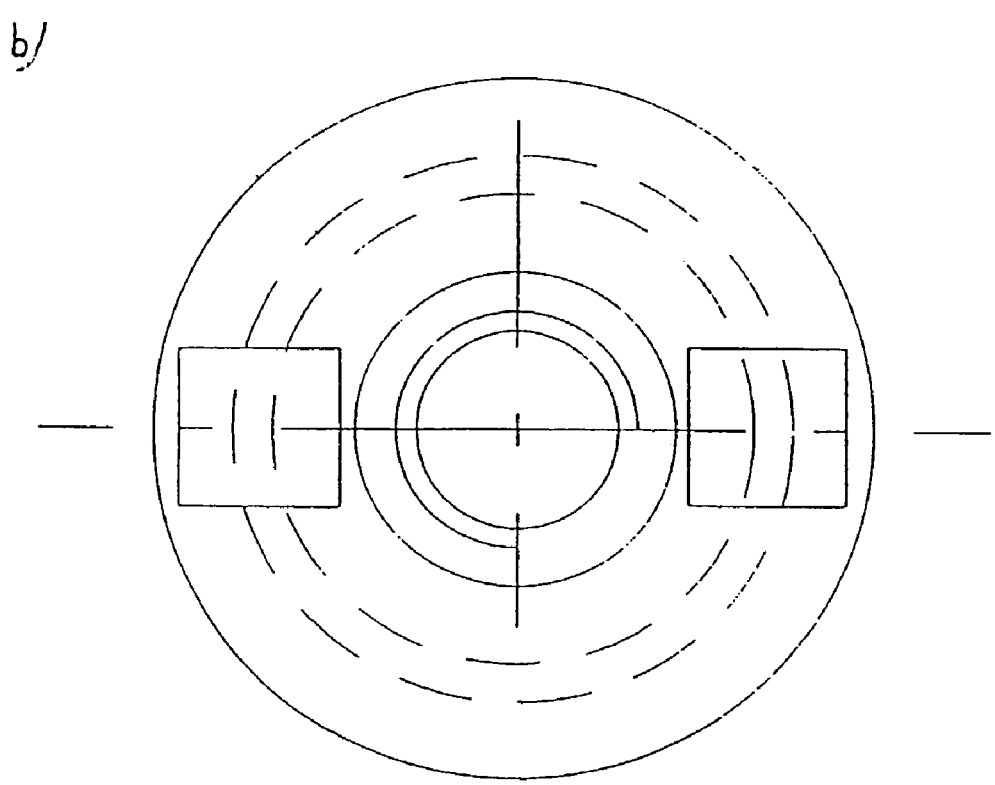

The basic principle of the method according to the present invention and the apparatus in which the method has been implemented is to raise and subsequently lower the temperature (or vice versa) locally in a cutaneous tissue area by supplying and draining heat until a predetermined temperature has been reached. After this temperature has been reached heat is no longer supplied or drained and the temperature in the cutaneous tissue will consequently change, i.e. decrease or increase depending on whether heat was supplied or drained. The temperature change is followed (recorded) in time until the temperature before supplying or draining is reached.

As the amount of heat supplied to or drained by the blood flow is proportional to the temperature difference between the tissue and the streaming blood the temperature of the cutaneous tissue will fall exponentially in time (Midttun et al. 1996). The rate constant, k, for this decrease/increase in temperature is under ideal measuring conditions solely dependent on the rate of blood flow.

Once the rate constant has been determined the flow rate is evaluated by the Kety-relation, as expressed for instance in Midttun et al. 1996, which correlates to the flow rate, f, and the rate constant, k, in the following manner:

$$f = k \cdot \lambda \cdot 100 \cdot (ml \cdot (100 \ g \cdot min)^{-1})$$

wherein λ termed as the tissue to blood partition coefficient, is a constant, which by experiments is found to be substantially equal to 0.954 (ml·g$^{-1}$). In practical situations and also in the experiments disclosed in this patent application a value of λ=1.0 is used.

Compared to prior art methods, which has been based only on heat wash-out, the method according to the present invention besides using a quasi stationary approach also makes use of heat wash-in (after-cooling) in order to compensate for a temperature dependence of the hydrodynamic conductance in blood vessels in the tissue as the blood flow rate will change with the temperature (Midttun et al. 1996).

A very important aspect of the present invention is the thermostating of the locally heated tissue's ambience to the same temperature as the temperature of the locally heated tissue. This is done in order to minimise the amount of heat conducted between the heated tissue and the ambience to that and the central measuring disc.

In a general simplified situation the amount of heat, Q, conducted from the skin to the ambience (or from the ambience to the skin) may be evaluated by:

$$Q=K(T_{amb}-T_{tissue}),$$

(K being the heat transfer coefficient), which shows that if $T_{amb}=T_{tissue}$ then no heat will be conducted from (or to) the tissue to (or from) the ambience. By keeping the ambience at substantially the same temperature as the measuring area during heat wash-in and wash-out it is, ideally, assured that the measured temperatures are correlated, ideally, only to the thermal interaction between the tissue and the blood and the thermal interaction with the ambience is avoided.

This aspect is embodied in a preferred embodiment of the invention by a cap being thermally controlled by Peltier elements acting as heating/cooling elements. In this preferred embodiment, the probe has the heating/cooling elements placed solely in the cap, and has a moveable/arrangable metal bridge for heating or cooling of a measuring disc. This measuring disc which comprises a thermistor is placed in contact with the cutaneous tissue surface and in the initial period it is heated or cooled by the Peltier elements via the metal bridge until a steady state temperature is obtained.

DETAILED DESCRIPTION OF PREFERRED EMBODIMENTS OF THE INVENTION

Principle of the Probe:

In FIG. 1 a presently most preferred embodiment of the apparatus, the probe, according to the present invention is depicted. The probe, indicated by numeral 10, comprises a cap 15, a measuring disc 20a, two Peltier elements 25, 30 and a movable metal bridge 35. The bridge 35 has an threaded part 35a which interacts with a thread provided in the bridge so the bridge may be dislocated in vertical direction upon rotation. Two thermistors 40a and 40b are contained in the cap 15 and one thermistor 45 is contained in the measuring disc 20a.

Figure 8:
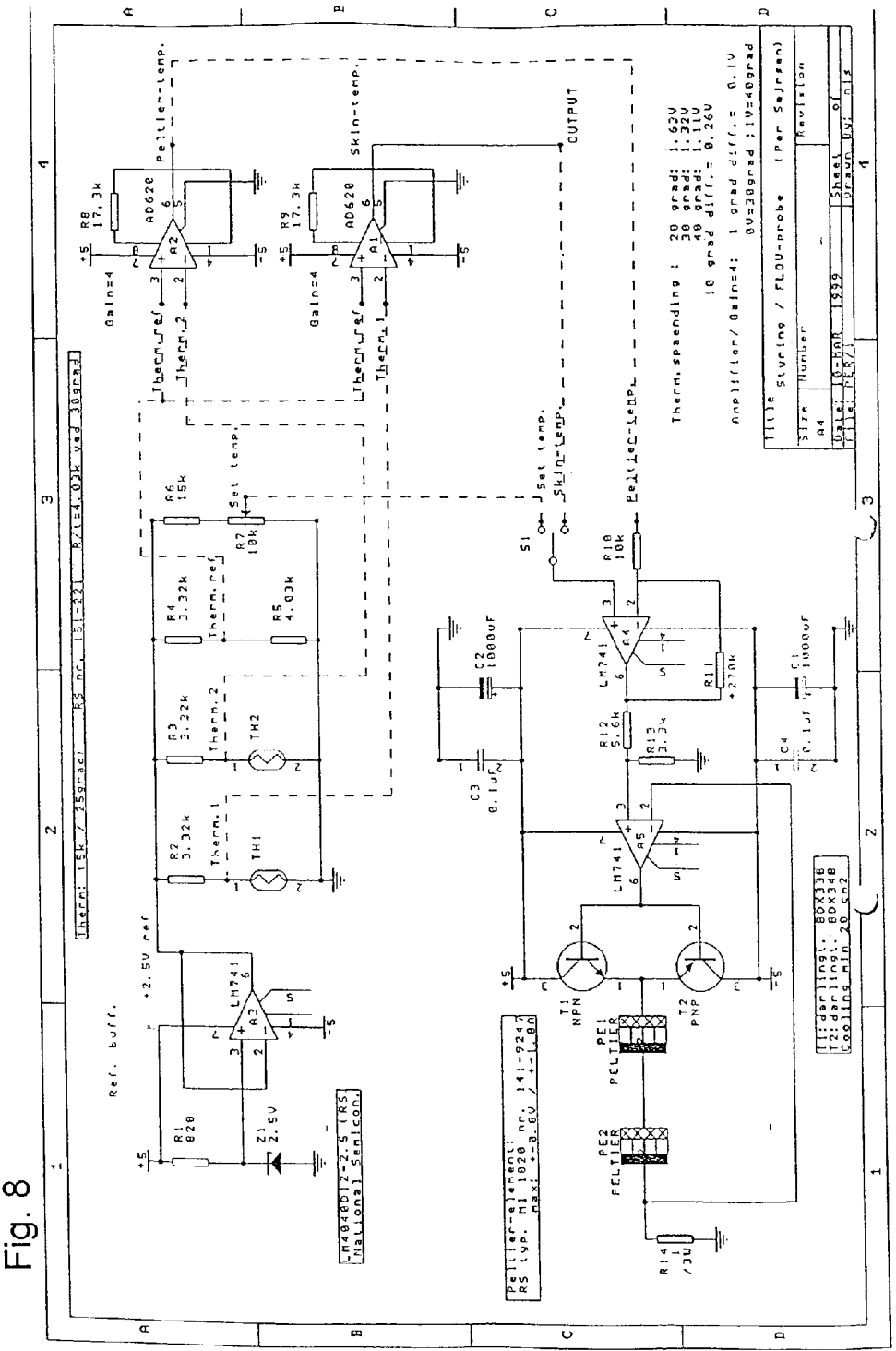
FIG. 8 is an electrical diagram showing the components and their wirings in a preferred embodiment of the electronics of the probe according to the present invention.

In the presently most preferred embodiment of the apparatus according to the present invention two Peltier elements, 25 and 30, are placed in the cap 15 and are being used as heating and cooling elements. The function of the cap is to heat or cool both the measuring disc containing the thermistor 45 and the cutaneous tissue in contact with the probe. Furthermore the cap 15 has to remove surplus of heat or cool to the surrounding air. The temperatures of the inner surface of the Peltier elements are controlled by the thermistors 40a and 40b in combination with a regulation amplifier A1 (FIG. 8).

A fixation ring 20b surrounds the measuring disc 20a having different heat transfer ability, i.e. having different heat transfer coefficient. This is embodied by manufacturing the disc 20 of two different materials whereof the material of the outer region 20b is chosen so that it has a low heat transfer coefficient (e.g. PVC) and the material of the central measuring disc 20a is chosen so that it has a high heat transfer coefficient (e.g. aluminium). By choosing so, only a smaller amount of heat will be conducted through the outer region 20b to the cap 15 whereby heat transfer may be controlled, at least partly, by the metal bridge 35 and partly by the cylinder part of the cap 15 being in contact with the tissue surface. 50 is an aluminium top for heat exchange with the surrounding air. 55 is the outer plastic cylinder.

The temperature of the tissue surface is registered in the heat conductive measuring disc 20a by the thermistor 45 contained in the disc 20a.

As the movable metal bridge 35 is in thermal contact with the cap 15 it can conduct heat or cold to the measuring disc with the thermistor and the cutaneous tissue in contact with the probe. After redrawing the metal bridge 35 it functions as a part of the cap. The metal bridge may be made of aluminium.

Measuring Principle:

Before measuring, the metal bridge 35 is placed in contact with the measuring disc 20a, which in turn is placed in contact with the surface of the cutaneous tissue. The measuring disc 20a and the skin area in contact with the probe are then heated or cooled to a chosen temperature, say $T_{upper}$. In this phase of the procedure, heat delivery (or extraction) is controlled based on the readings of the thermistors 40a, 40b placed in contact with the inner side of the Peltier elements 25, 30. When the chosen temperature, say $T_{upper}$ is reached, typically after a few minutes, then the metal bridge 35 is removed from the measuring disc 20a to the cap 15. In the following phase, the measuring phase, the two Peltier elements 25 and 30 are controlled based on (thermostated to) the temperature of the thermistor 45 in the measuring disc 20a. By controlling the Peltier elements in such a manner heat transfer from the (or to) the measuring disc 20a is eliminated by setting the temperature gradient between the disc 20a and the surrounding air equal to zero. The cap 15 as explained in the section "General description of the invention" does this setting of the temperature gradient in combination with the Peltier elements.

In the following phase the temperature decrease (or increase) in time is registered. In the first 10 to 30 seconds, typically, of this phase there will be a fast temperature equilibration between the heated (or cooled) cutaneous tissue and the measuring disc 20a. Thereafter the temperature will change as a mono-exponential decrease (or increase) in time. The rate constant of these changes is proportional to the blood flow rate in the cutaneous tissue in contact with the probe 10.

The initial fast temperature equilibration between the tissue and the measuring disc 20a is due to the thermal resistance between the skin and the measuring disc 20a being small and the diffusibility being high. The temperature difference present initially in this phase is produced by the heating (or cooling) procedure in the former phase. This temperature gradient will be reduced very fast when the metal bridge 35 is removed from the measuring disc 20a with thermistor 45 measuring the temperature decrease (or increase) towards the basis temperature, $T_{basis}$, as measured before the heating (or the cooling) procedure. It is important that the heat capacitance of the measuring disc 20a is small so that the thermal time constant is small whereby the influence on the measurement of the temperature changes in the tissue is limited.

In the initial phase the Peltier elements in the cap are in thermal contact with the central measuring disc via a metal bridge. This has the form of a screw with a movement of distance of around 0.8 mm.

Other preferred solutions are electro-mechanic or hydraulic.

After heating or cooling of the measuring area thereby providing a temperature change of around 1–5° C. the metal bridge is redrawn 0.8 mm and it is now included in the thermostated cap controlled to keep the temperature similar or equal to the measuring disc. This is done to minimise the heat loss or heat uptake from the surroundings to the central measuring disc.

Electronics:

For the Peltier elements 25, 30 an effect amplifier, having a range of a few Voltage(<±5V) and a current of about ±2A was applied.

There has to be a current limitation to protect the Peltier elements 25, 30 (max. ±1.8A). It has been found that it is appropriate to have a constant current source. A correction for Voltage errors, i.e. voltage variation, has to be changeable in the two measuring phases. The gain/time constant has to be fitted taking the demand of stability for the regulation loop into account.

The thermistors 40a and 40b should have the same characteristics (R=f(t)). The linearisation of the voltage to temperature relation can be done either analogously or in a connected computer.

Furthermore, the metal bridge may eventually be moved by response to an electronic controller and in that case there shall be a loop for moving the metal bridge into the two positions.

Comments on Dimensions:

In the following a brief discussion of the criteria applied for selecting various types of articles used in the probe 10 is presented. Different suggestions are made for some of the crucial articles. These suggestions should not be construed as being the only choices, as a person skilled in the art easily would be able to replace articles in case the probe is utilised in another measuring environment.

The Peltier Elements 25, 30:

By experiments it is found that the effect used for heating the probe should not exceed approximately 500 mW. Furthermore, it has been found by experiments according to the present invention that in order to produce a constant temperature level in the tissue an effect of less than 100 mW is necessary.

A proper type of the Peltier elements is a RadioParts type MI 1020T, which has a maximal cooling effect of 900 mW at a current of 1.8 A. The dimension of the Peltier elements is 4 times 4 times 2 mm.

Figure 9:
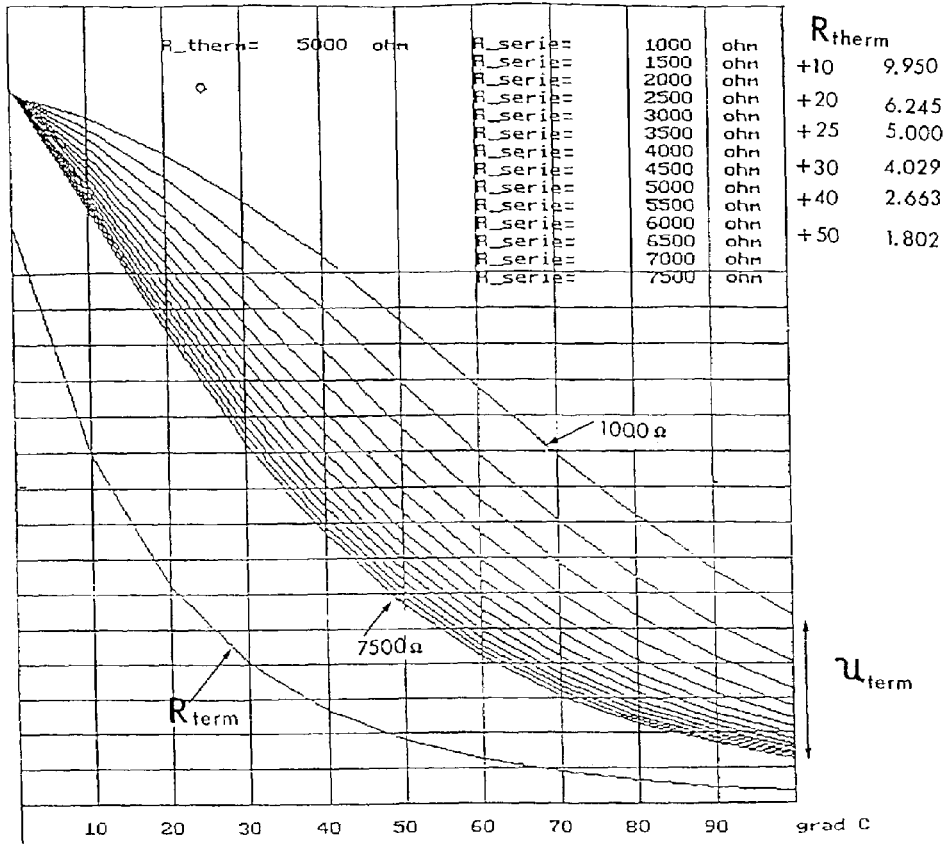
FIG. 9 shows the linearity between amperage and temperature in a presently preferred temperature interval.
Figure 9:
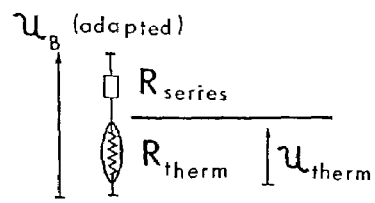

The Thermistors 40a, 40b and 45:

The thermistors 40a, 40b and 45 must be small and fast reacting in giving a dynamic and stable regulation loop around the Peltier elements 25, 30 to follow the tissue temperature. The rapidity has to be compared to that of the Peltier elements 25, 30 at maximal effect delivery. Thus, the thermistors shall have a small heat capacity and good heat conduction ability to the surroundings (in accordance with a small size). Radio Parts nr. 151-221-5 kOhm NTC is usable. The linearity between temperature and current intensity over intervals of more than 10° C. at different values of resistance is presented in FIG. 9.

The Measuring Disc 20a:

It is important that the temperature registered by the thermistor 45 in the measuring disc 20a is as close as possible to the tissue temperature. This is only the case if the involved thermal resistance between tissue and the measuring disc 20a is negligible. If the resistance is large there will be no heat transport between tissue and measuring disc 20a and the reading of the thermistor 45 will not be the temperature of the tissue. Therefore a good thermal contact between the tissue and the measuring disc 20a is very important. The heat capacity of the measuring disc 20a has to be small and the heat conductance from the disc 20a to the surrounding parts of the probe has to be small. In order to express an average temperature of the underlying tissue by the thermistor 45 the heat conduction ability of the heat disc 20a shall be very good. The measuring disc 20a shall be fixed in the probe 15 thermally well isolated from the rest of the probe 15. The fixation ring 20b is therefore made of plastic with a low heat conduction coefficient.

The inner surface of the Peltier elements 25, 30 shall have a good heat conduction to get a uniform temperature distribution. The heat capacitance of the metal bridge 35 is found to play only a secondary role.

The Outer Cap 15:

The temperature of the upper part of the cap 15 shall, ideally, be constant and substantially the same as the temperature of the room in which the measurement is performed. Therefore, the cap 15 can have a great heat capacity and a large outer surface, which may ideally be black and rough to secure a good heat transfer to the surroundings from the aluminium top 50.

The Metal Bridge 35:

During the heating or cooling phase the metal bridge 35 is placed in contact with the measuring disc 20a. In the measuring phase the metal bridge 35 is redrawn to its retracted position in the cap 15. This is in the preferred embodiment done mechanically. Other mechanisms are possible such as air pressure or a procedure performed by electromagnetism.

Principle for Measurement of Cutaneous Blood Flow Rate by Heat Wash-Out and Heat Wash-In After an initial period of heating or cooling, the change in the surface temperature of the cutaneous tissue in time is measured by the thermistor 45. The thermistor is placed in a small metal disc 20a placed in direct contact with the cutaneous tissue surface.

During the initial heating or cooling of the measuring disc 20a, a metallic thermal bridge 35 is placed between a surrounding cap 15 and the measuring disc 20a. This cap 15 contains two Peltier elements 25, 30 for heating or cooling. During the following heat wash-out or heat wash-in period this thermal bridge 35 is withdrawn to the cap 15.

The thermostated cap 15 has the aim to minimise the heat loss to the surroundings of the measuring disc 20a during a heat wash-out or a heat wash-in period. This is done by thermostating the cap 15 to keep the same temperature as the thermistor 45 in the measuring disc 20a during the measuring period of heat wash-out or heat wash-in.

The thermistor 45 in the measuring disc 20a thus measures the temperature of the cutaneous tissue surface during the heat wash-out or heat wash-in.

The thermal capacitance of the measuring disc 20a with thermistor 45 has to be small compared to that of the measuring area of the cutaneous tissue.

If the measured wash-out rate or wash-in rate shall be a measure of blood flow rate then the heat transport rate between the cutaneous tissue and the measuring disc 20a with thermistor 45 has to be much greater than the elimination rate of heat by blood flow.

The Heat Wash-Out/Heat Wash-In Method for Measurement of Cutaneous Tissue Blood Flow Rate—Procedure for Measurement:

In the following the measuring procedure is described by the item list below. The measuring is initiated by:
1. Registration of the temperature by the thermistor in the measuring disc of the measuring probe 10 (the cutaneous tissue surface temperature in the measuring area) for 3–5 min to obtain a steady state, defined as the basis temperature, $T_b$.
2. Heating 2–5° C. until a steady state temperature level is obtained (3–5 min). Then registration of the heat wash-out in time until the basis temperature $T_b$ as measured before heating is reached.
3. Registration of the temperature by the thermistor in the measuring disc of the measuring probe (the cutaneous tissue surface temperature in the measuring area) for 3–5 min to obtain a steady state, defined as the basis temperature, $T_b$.
4. Cooling 2–5° C. until a steady state temperature level is obtained (3–5 min). Then registration of the heat wash-in in time until the basis temperature $T_b$ as measured before heating is reached.

Calculations:

The following examples show how to evaluate the blood flow rate. Initially, the rate constant is determined:
1. Calculation of the rate constant, $k_{hwo}$, for heat wash-out: $k_{hwo} = dT_{hwo} \cdot ((T_h - T_b) \cdot \ln 2 / T_{1/2}$, where $dT_{hwo}$ is the temperature fall in the time interval dt and $T_h$ is the temperature obtained in the steady state by heating and $T_b$ is the temperature as measured before heating.

Then the blood flow rate is calculated:
2. The blood flow rate, $f_{hwo}$, is then calculated as: $f_{hwo} = k_{hwo} \cdot 1 \cdot 100 (\text{ml} \cdot (100 \text{ g} \cdot \text{min})^{-1})$.

The procedure is repeated, now for heat wash-in, i.e.:
3. Calculation of the rate constant, $k_{hwi}$, for heat wash-in: $k_{hwi} = dT_{hwi} \cdot ((T_b - T_c) \cdot dt)^{-1} = \ln 2 : T_{1/2}$, where $dT_{hwi}$ is the temperature increase in the time interval dt and $T_c$ is the temperature obtained in the steady state by cooling and $T_b$ is the temperature as measured before cooling.

Again the blood flow rate is evaluated, now for heat wash-in, i.e.:
4. The blood flow rate, $f_{hwi}$, is then calculated as: $f_{hwi} = k_{hwi} \cdot 1 \cdot 100 (\text{ml} \cdot (100 \text{ g} \cdot \text{min})^{-1})$ The actual blood flow rate is determined as the average between $f_{hwo}$ and $f_{hwi}$, i.e.:
5. Calculation of the numerical mean value of the registered values $f = (f_{hwo} + f_{hwi}) : 2$, which is presumed to give a value of the cutaneous blood flow rate at the basis temperature before heating or cooling.

Comments on the Blood Flow Rate Determination Procedure:

The following observations/acceptances have been found to be of such a nature that they may influence the measuring principle according to the present invention:
1. When registrations are performed in cutaneous areas without arterio-venous anastomoses, AVA's, there will be a higher value of blood flow rate during heat wash-out and a lower value during heat wash-in than in a situation with unchanged temperature.
2. In cutaneous areas with many AVA's, such as in fingers and toes, there will be a small difference between the blood flow rate measured during heat wash-out or heat wash-in during a positive heat balance with blood flow in the AVA's. During a negative heat balance without blood flow in the AVA's these areas will be equal to areas without AVA's and a mean value, f, between values obtained by heat wash-out and heat wash-in can be used.

Experimental Section

In the following section, a review of experiments performed by the probe and the method according to the present invention will be presented. The experiments are performed as comparative experiments, and examples are disclosed for measurement performed by the apparatus and method according to the present invention and measurement performed with the prior art probe discussed in the section "Introduction to the invention". The measurements were performed simultaneously on the pulp of both thumbs on two subjects, subject A and subject B. The following measurements were done after changing side of the apparatus.

In the measurements shown below the upper temperature reached during heating was 40° C.

Measurement of f on subject A on the pulp of both thumbs (results given as ml$(100 \text{ g} \cdot \text{min})^{-1}$) and $\chi$ is the average of the four determinations of f).

| Prior art probe (at 40° C.) | Heat wash-out/heat wash-in probe (at 40° C.) |
|---|---|
| Right: 120.4, and 103.7 | left: 147.0, and 112.0 |
| Left: 105.6, and 107.3 | right: 83.5, and 99.0 |
| $\chi = 109.25$ | $\chi = 110.38$ |

Measurements of f on subject B on the pulp of both thumbs (results given as ml$\cdot(100 \text{ g} \cdot \text{min})^{-1}$) and $\chi$ is the average of the four determinations of f).

| Prior art probe (at 40° C.) | Heat wash-out/heat wash-in probe (at 40° C.) |
|---|---|
| Right: 168.8, and 144.2 | left: 165.0, and 181.0 |
| Left: 185.5, and 143.5 | right: 181.0, and 147.0 |
| $\chi = 160.5$ | $\chi = 168.5$ |

Measurements of f on subject B on the pulp of the thumbs (results given as ml$\cdot(100 \text{ g} \cdot \text{min})^{-1}$) and $\chi$ is the average of the six determinations of f).

| Prior art probe (at 40° C.) | Heat wash-out/heat wash-in probe (at 40° C.) |
|---|---|
| Right: 173.6, 150.0, and 161.6 | left: 161.0, 138.6, and 187.0 |
| Left: 154.8, 150.0, and 155.2 | right: 165.0, 173.0, and 165.0 |
| $\chi = 157.5$ | $\chi = 164.9$ |

Measurements of f on the forearm at various temperatures with a lead shield placed distally to the probe in order to eliminate the blood flow in the venous rete on the forearm.

Measurements of f on subject A in four days (results given as ml$\cdot(100 \text{ g} \cdot \text{min})^{-1}$).

| | | |
|---|---|---|
| Cooling | 5° C., | f = 10.8, 14.4, 19.6, and 7.6 |
| " | 4° C., | f = 12.1, 15.7, 19.3, and 17.3 |
| " | 3° C., | f = 13.8, 18.7, 21.6, and 18.2 |
| " | 2° C., | f = 16.5, 19.1, 23.1, and 19.8 |
| " | 1° C., | f = 20.4, 23.9, and 20.6 |
| " | 0° C., | f = 16.1, 19.2, and 22.3 |
| Heating | 1° C., | f = 18.2 |
| " | 2° C., | f = 20.2, 21.2, 19.8, 26.3, and 24.7 |
| " | 3° C., | f = 22.4, 22.3, 27.4, and 25.7 |
| " | 4° C., | f = 23.1, 23.9, 28.9, and 25.7 |
| " | 5° C., | f = 26.6, 27.7, 31.5, and 29.5 |

Figure 5:
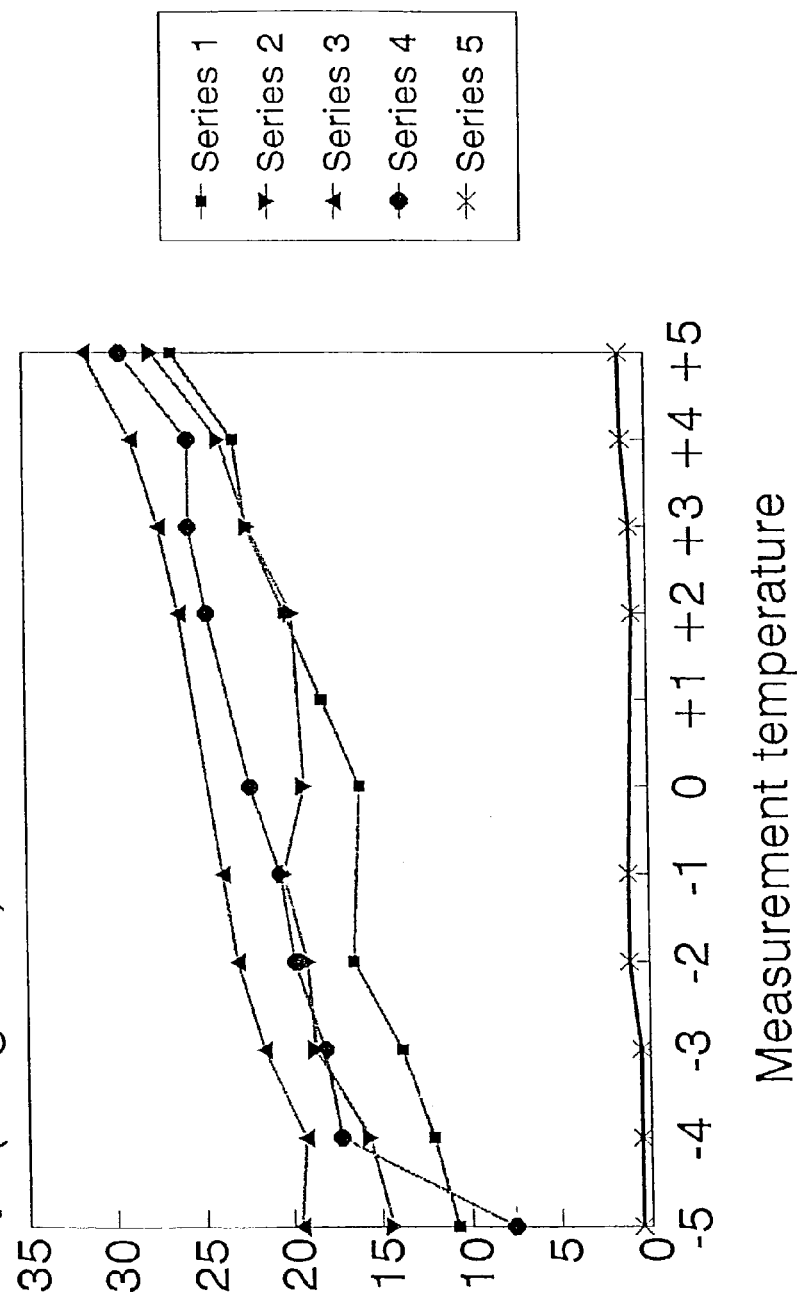
FIG. 5 shows graphical measurements of blood flow rate performed with the probe according to the present invention, the measurements are carried out on the forearm of a test-person at various temperature levels.

The results are presented in FIG. 5.

Measurements on the forearm at various temperatures during blood flow cessation performed with a blood pressure cuff inflated to 200 mmHg on the upper arm and with a lead shield placed distally to the probe in order to eliminate the blood flow in the venous rete on the forearm.

Measurements on subject A in three days (results given as ml·(100 g·min)$^{-1}$).

| | | |
|---|---|---|
| Cooling | 5° C. | f = 0.5 |
| " | 4° C. | f = 0.5 |
| " | 3° C. | f = 0.5 |
| " | 2° C. | f = 1.1 |
| " | 1° C. | f = 1.1 |
| Heating | 1° C. | f = — |
| " | 2° C. | f = 0.8 |
| " | 3° C. | f = 0.9 |
| " | 4° C. | f = 1.3 |
| " | 5° C. | f = 1.4 |

The results are presented in FIG. 5.

Measurements on the pulp of the thumb at various temperatures.

Measurements on subject A in five days (results given as ml·(100 g·min)$^{-1}$).

| | | |
|---|---|---|
| Cooling | 5° C., | f = 83.5, 83.0, 83.0, and 95.0 |
| " | 4° C., | f = 93.0, and 107.0 |
| " | 3° C., | f = 115.0, 96.0, and 87.0 |
| " | 2° C., | f = 103.0, 99.0, and 103.0 |
| " | 1° C., | f = 93.0, 66.0, 87.0, and 107.0 |
| Heating | 0° C., | f = 154.0, and 103.0 |
| " | 1° C., | f = 119.0, and 84.0 |
| " | 2° C., | f = 154.0, 115.0, and 110.0 |
| " | 3° C., | f = 126.0, 115.0, and 87.0 |
| " | 4° C., | f = 154.0, and 93.0 |
| " | 5° C., | f = 119.0, and 107.0 |

Figure 6:
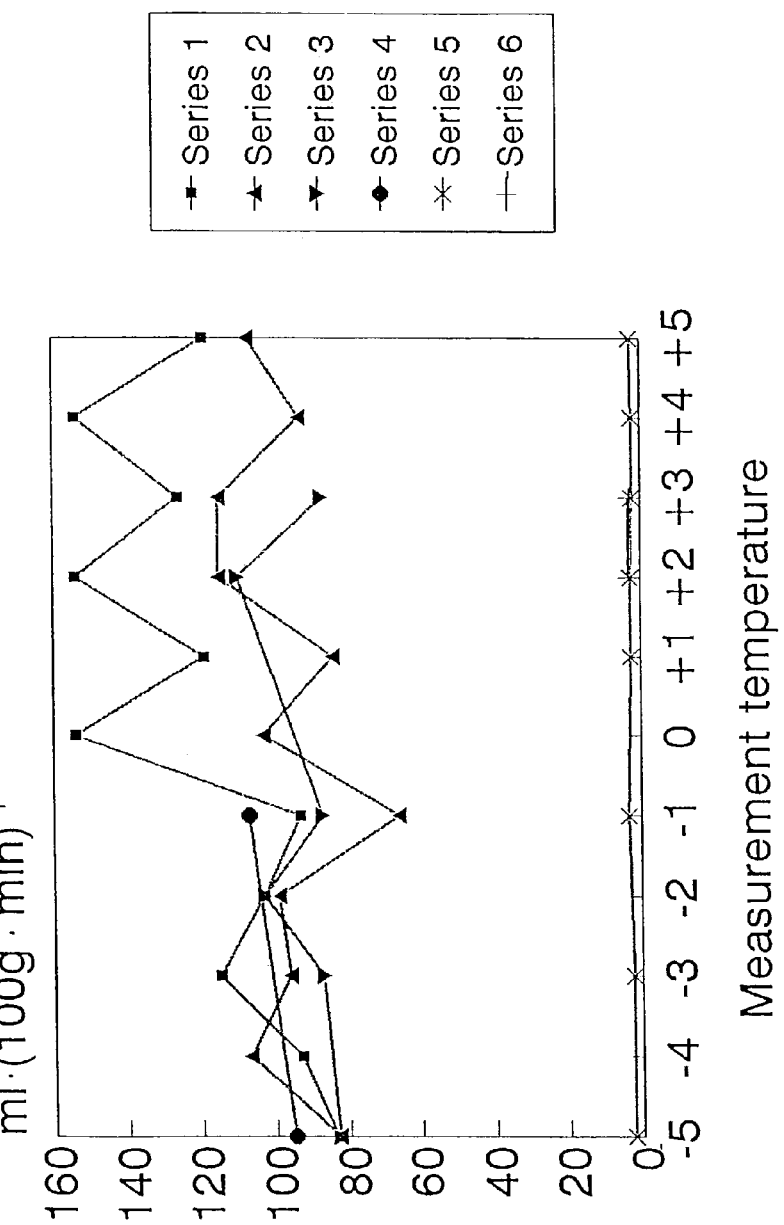
FIG. 6 shows graphical measurements of blood flow rate performed with the probe according to the present invention, the measurements are carried out on the pulp of the thump of a test-person at various temperature levels and during blood flow cessation.

The results are presented in FIG. 6.

Measurements on the pulp of the thumb at various temperatures during blood flow cessation performed with a blood pressure cuff inflated to 200 mmHg on the upper arm.

Measurements on subject A in three days (results given as ml·(100 g·min)$^{-1}$).

| | | |
|---|---|---|
| Cooling | 5° C. | f = 2.3 |
| " | 3° C. | f = 2.3 |
| " | 1° C. | f = 3.4 |
| Heating | 1° C. | f = 2.8 |
| " | 2° C. | f = 2.8, and 3.1 |
| " | 3° C. | f = 2.4, and 3.1 |
| " | 4° C. | f = 2.4 |
| " | 5° C. | f = 2.9 |

The results are presented in FIG. 6.

Measurements on the pulp of the thumb at elevation of the hand.

Measurements on subject A. The region was heated 2° C. at all measurements (results given as ml·(100 g·min)$^{-1}$).

| | |
|---|---|
| Heart level: | f = 87.0 |
| Elevation 45 cm: | f = 21.6 |
| Heart level: | f = 84.0 |
| Elevation 70 cm: | f = 9.0 |
| Heart level: | f = 73.0 |

Figure 7:
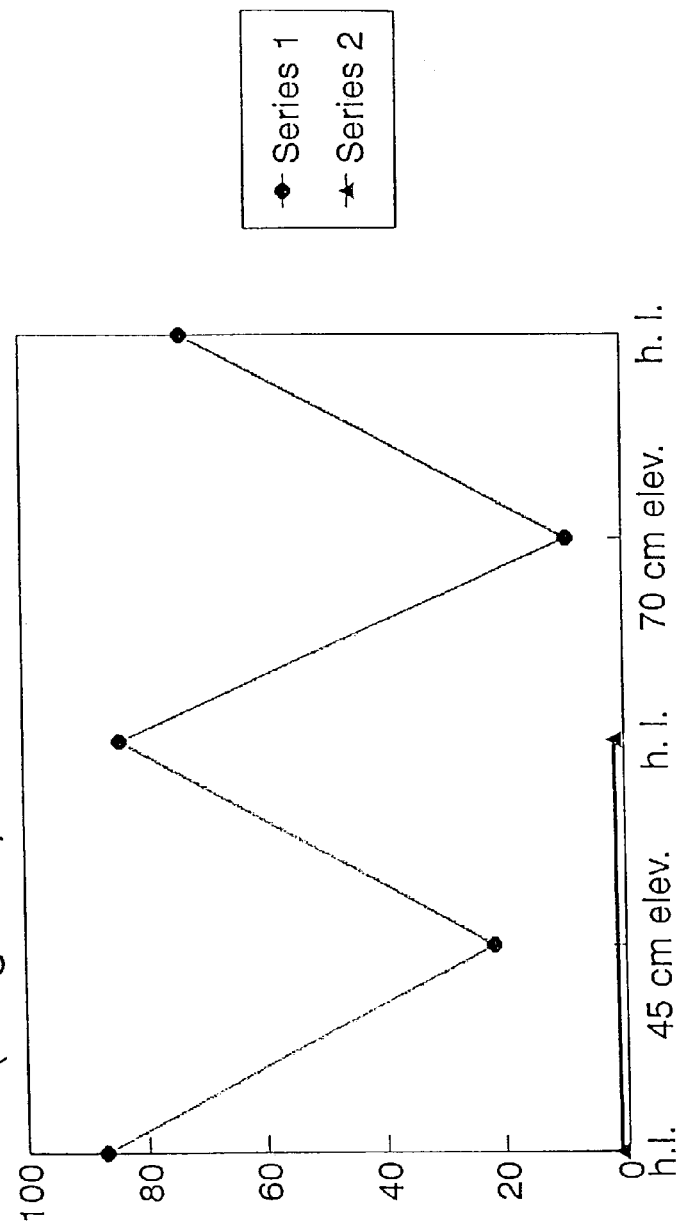
FIG. 7 shows graphical measurements of blood flow rate performed with the probe according to the present invention, the measurements are carried out at different positions of a test-person's thump and with the other hand in ice-water.

The results are presented in FIG. 7.

Measurements on the pulp of the thumb before and after placing the other hand in ice water.

Measurements on subject A in two days (results given as ml·(100 g·min)$^{-1}$).

| | |
|---|---|
| Measurement performed at cooling 1° C. | f = 1.3 |
| Measurement performed at heating 2° C. | f = 1.6 |

The results are presented in FIG. 7.

Measurements on Polystyrene Foam

Measurements performed in two days (results given as ml·(100 g·min)$^{-1}$).

f=2.0, 1.9, and 1.9.

Concluding Evaluation

The measuring results obtained with the new constructed equipment for measurement of the cutaneous blood flow rate by the heat wash-out/heat wash-in method have given results in very good agreement with those registered by the prior art probe, which only uses the heat wash-out principle. The prior art probe has previously been compared to the $^{133}$Xe-wash-out method in simultaneous experiments showing a very high correlation of the results at variation of the temperature of the probe. The heat wash-in/wash-out probe according to the present invention gives the possibilities of performing measurement at temperature levels below the undisturbed cutaneous temperature.

Comparative measurements on 2 subjects were done for comparison of results obtained by the two probes placed on each pulp of the thumb and 2–3 registrations were performed before and after side change.

Measurements on the forearm at various temperatures were performed with a lead shield placed on the skin distal to the probe to make compression of the skin eliminating the blood flow in the subcutaneous venous rete on the forearm. It was observed that the blood flow rate increased at increasing temperature. This is in accordance with observations obtained previously by the prior art probe.

As realised from the data presented in FIG. 5 the dependency of the blood flow rate varies substantially linearly with respect to the temperature reached during heat wash-in and heat wash-out. This linear dependency is the background for—and justifies—the use of a mean value of the blood flow rate being determined on the flow rate found during heat wash-in and during heat wash-out.

The results from measurements on the forearm during blood flow cessation gave very low values, as presented in FIG. 5. This is in accordance with the results obtained by the prior art probe in the previous experiments.

Measurements on the pulp of the thumb at various temperatures of the probe showed as previously registered by the prior art probe, that the blood flow rate in the finger pulp increases little at increasing temperature of the probe.

The results from measurements on the pulp of the thumb during blood flow cessation showed very low values in accordance with previous observations with the prior art probe. The results are presented in FIG. 6.

Measurements on the pulp of the thumb during elevation of the hand to 45 cm and 70 cm above heart level gave as expected reductions in the blood flow rate in accordance to the reduction in perfusion pressure at the two levels, as seen in FIG. 7.

Measurements on the pulp of the thumb with the other hand placed in ice water showed normal values before and values as low as 1.3 and 1.6 ml·(100 g·min)$^{-1}$ during this procedure. These values are comparable with those measured during blood flow cessation.

Measurements with the probe placed on polystyrene foam were performed to demonstrate a zero value of the probe as the probe has a small heat loss to the surroundings. This heat loss is about the same size as that obtained on cutaneous tissue during blood flow cessation.

Conclusions:

The new developed equipment based on the heat wash-out/heat wash-in principle has given expected and fully satisfying results. The results are in accordance with those obtained by the prior art probe.

Expected results were found for changes in temperature of the probe on the forearm, for changes of the position of the measuring area above heart level, and for changes when the other hand was placed in ice water.

The heat wash-in/wash-out method applied for determining the blood flow rate in the previous examples has the possibility to determine the blood flow rate at normal tissue conditions, i.e. at undisturbed temperatures as an average to the prior art probe which determined the blood flow rate at a temperature being different from the undisturbed tissue temperature.

Other Applications of the Invention

In the following different areas for application of the heat wash-out/heat wash-in method for instance in diagnostics, in evaluation of treatment effect, and in research are described as a list of items. Each item in the list of items comprises the area of application and to what extend the probe is applicable in the area.

Atheromatoses/atheroscleroses in leg arteries: Localisation, control of treatment effect of surgery or balloon dilatation and in supervision of the blood perfusion in the post operative period.

Amputation: Determination of the level for amputation, before amputation.

"White fingers": A hereditary disease or it is acquired by use of vibrating tools.

Skin diseases: For example psoriasis, with measurements before and after a treatment as a control of the effect of the treatment.

Burn injuries: Evaluation of the lesion degree of a burn injury, and also in evaluation of the effect of a treatment.

Cold injuries: Evaluation of the lesion degree of a cold injury, and in evaluation of the effect of a treatment.

Skin grafts: Evaluation of the revascularisation of a graft.

During surgery: Used for measurement of blood flow rate in organs or tissues during surgery, for example in lever, kidney, intestine etc., with the probe inserted in a steril plastic foil.

Heart diseases: Measurement of blood flow rate in the pulp of a thumb or a toe after a myocardial infarction (AMI) in order to register when the sympathetic activity is increased and when it becomes normalised, as an expression of a normalisation of the blood circulation system. Furthermore, to demonstrate an eventual effect of a treatment.

Metabolic disorders: Measurement of blood flow rate in the pulp of the thumb and in other skin areas in thyreotoxicose and myxoedema to estimate an expression of the metabolic rate and to follow the effect of a treatment.

Varicose veins: Evaluation of treatments of ulcers coursed by varicose veins, including pressure bandages and surgical interventions.

Supervision: Supervision of patients during general anaesthesia to evaluate the level of the sympathetic activity/the functional state of the blood circulation system. Supervision of patients in intensive care units to evaluate the sympathetic activity level.

Premature babies and children: Supervision of blood circulation system in prematures and children.

Diabetics: Measurement in skin areas with threatened gangrene. Evaluation of the degeneration of the sympathetic system at diabetes.

Temperature regulation: Investigations of mechanisms involved in the temperature regulation during heat load and cold load, and during muscular exercise at various loads.

Other Applications for Which the Probe and the Method According to the Present Invention may be used Advantageously The present invention has until now been described with focus on the application to measuring of blood flow rate in a human body. Although this choice of focus the invention may advantageously be applied to other fields of measurements as well. Such areas of applicability of the heat wash-out/heat wash-in method for measurement of flow rates will be described in the following and in particular the measurement of flow rate in pipelines will be addressed.

In a first case, the probe is applied to the outer surface of a tube conducting the fluid which flow rate has to be measured. Heat is subsequently applied to/drained from the fluid in the same manner as when flow rate of blood is measured in human tissue.

In another case, the measuring principle may very advantageously be used for registration of flow rate of a fluid in a pipeline such as in water supply, in sewers, in district heating and in an oil line. This can be established by a measuring area comprising a bundle of thin tubes, having a diameter of app. 1 mm., placed in parallel in a small block, having a dimension of around 0.5–1 cm, being in contact with the measuring probe. The fluid flow shall pass through the thin tubes being placed in the direction of the fluid flow in the pipeline. This unit constitutes the measuring apparatus and by placing it through a bore hole in the wall of a pipeline it is possible by heating or by cooling to make a measurement of the flow rate of the fluid analogously to the measurement of the blood flow in tissue. From the knowledge of the diameter of the pipeline it will be possible to calculate the volume flow rate in the pipeline.

The invention claimed is:

1. An apparatus for measuring the flow rate of a fluid confined by a wall member, which apparatus comprises:
    contacting means for contacting the wall member, the contacting means being formed of a material having a first heat transfer coefficient so that heat may be exchanged between the wall member and the contacting means,
    heating means for supplying heat to and draining heat from the contacting means so that heat is being supplied to the wall member when heat is being supplied to the contacting means and so that heat is being drained from the wall member when heat is being drained form the contacting means,
    sensor means for sensing the temperature of the contacting means, and
    processor means adapted to perform the determination of the flow rate of said fluid on the basis of two subsequently registered progressions of the temperature of the contacting means, one of said registered temperature progressions being a temperature decrease and another of said registered temperature progressions being a temperature increase.

2. An apparatus according to claim 1, further comprising encapsulating means encapsulating the heating means and encapsulating partly the contacting means, the encapsulating means having an outer surface whereof at least a part of it is exposed to the surroundings when the contacting means is contacting the wall member.

3. An apparatus according to claim 1, further comprising sensor means for sensing the temperature of the encapsulating means and means adapted to control the temperature of the encapsulating means in such a manner that the temperature of the encapsulating means is at least substantially equal to the temperature of the surface of the wall contacted by the contacting member.

4. An apparatus according to claim 1 wherein the contacting means has at least two regions with different heat transfer coefficient at least concentrically arranged thereby defining an inner and an outer region.

5. An apparatus according to claim 4, wherein the heat transfer coefficient of the outer region of the contacting means is smaller than the heat transfer coefficient of the inner region of the contacting means.

6. An apparatus according to claim 1 further comprising processor means adapted for controlling the heating means so that the heat supplied by and/or drained by heating means is supplied/drained in a predetermined manner.

7. An apparatus according to claim 6, wherein processor means are adapted to perform the determination of the flow rate of said fluid as an average of a flow rate determined on the basis of the registered temperature decrease and a flow rate determined on the basis of the registered temperature increase.

8. An apparatus according to claim 1, wherein the heating means comprises at least two heating means one heating means for supplying heat and one heating means for draining heat.

9. An apparatus according to claim 1, wherein the heating means is/are of a Peltier type.

10. An apparatus according to claim 1, further comprising bridging means for providing thermal contact between the heating means and the contacting means, said bridging means being arrangable for enabling said thermal contact and being arrangable for disabling said thermal contact.

11. An apparatus according to claim 10, wherein the bridging means has the form of a bridge being movable between a first position in which it is in thermal contact with both the heating means and the contacting means and a second position in which it is in thermal contact with either the heating means or the contacting means at one time and does not simultaneously contact both.

12. A method for measuring the flow rate of a fluid confined by a wall member, which method comprises
    supplying heat locally to the wall member until a prescribed upper temperature relating to the temperature of the locally heated wall member is achieved,
    recording progression of a temperature relating to the wash-out of heat by the fluid,
    draining heat locally from the wall member until a prescribed lower temperature relating to the locally cooled wall member is achieved,
    recording the progression of a temperature relating to the wash-in of heat by the fluid,
    determining based on the progression of temperature during wash-in and wash-out the flow rate of the fluid.

13. A method according to claim 12, wherein the prescribed upper temperature reached when supplying heat is the steady state temperature.

14. A method according to claim 12, wherein the prescribed lower temperature reached when draining heat is the steady state temperature.

15. A method according to claim 12, wherein heat is drained from the wall member in such a manner that the temperature of the wall member evolves in a predetermined manner.

16. A method according to claim 12, wherein heat is supplied to the wall member in such a manner that the temperature of the wall member evolves in a predetermined manner.

17. A method for measuring the flow rate according to claim 12, further comprising the step of controlling the temperature above the wall member during heat wash-out in such a manner that heat is substantially not drained from the wall member to the exterior.

18. A method for measuring the flow rate according to claim 12, further comprising the step of controlling the temperature above the wall member during heat wash-in in such a manner that heat is substantially not supplied to the wall member from the exterior.

19. A method for determining the flow rate utilizing the step according to claim 12, further comprising the steps of:
    determining a flow rate constant relating to heat wash-in and a flow rate constant relating to heat wash-out, the determination of the flow rate constants being based on the recorded temperature progressions corresponding respectively to heat wash-in and heat wash-out;
    determining a heat wash-in fluid flow rate relating to flow rate during heat wash-in, the determination of the fluid flow rate being based on the corresponding flow rate constant;
    determining a heat wash-out fluid flow rate relating to flow rate during heat wash-out, the determination of the fluid flow rate being based on the corresponding flow rate constant; and
    determining a mean fluid flow rate based on averaging the heat wash-in and heat wash-out fluid flow rate.

20. An apparatus for measuring the flow rate of a fluid confined by a wall member, which apparatus comprises:

contacting means for contacting the wall member, the contacting means being formed of a material having a first heat transfer coefficient so that heat may be exchanged between the wall member and the contacting means;

heating means for supplying heat to and draining heat from the contacting means so that heat is being supplied to the wall member when heat is being supplied to the contacting means and so that heat is being drained from the wall member when heat is being drained from the contacting means; and bridging means for providing thermal contact between the heating means and the contacting means, said bridging means being arrangable for enabling said thermal contact and being arrangable for disabling said thermal contact.

* * * * *